United States Patent [19]

Withycombe et al.

[11] 4,263,332

[45] * Apr. 21, 1981

[54] USE OF 2(2'-METHYLTHIOPROPYL)-4,5-DIMETHYL-Δ³-THIAZOLINE TO AUGMENT OR ENHANCE THE AROMA OR TASTE OF MASHED POTATO FLAVOR OR MASHED POTATO FLAVORED FOODSTUFFS

[75] Inventors: Donald A. Withycombe, Lincroft; Braja D. Mookherjee, Holmdel; Cynthia J. Mussinan, Bricktown; Manfred H. Vock, Locust; Christopher Giacino, Califon, all of N.J.

[73] Assignee: International Flavors & Fragrances Inc., New York, N.Y.

[ * ] Notice: The portion of the term of this patent subsequent to Mar. 17, 1998, has been disclaimed.

[21] Appl. No.: 105,887

[22] Filed: Dec. 21, 1979

Related U.S. Application Data

[60] Division of Ser. No. 17,579, Mar. 5, 1979, which is a continuation-in-part of Ser. No. 730,156, Oct. 7, 1976, abandoned.

[51] Int. Cl.³ .............................................. A23L 1/226
[52] U.S. Cl. ..................................................... 426/535
[58] Field of Search ....................................... 426/535

[56] References Cited

U.S. PATENT DOCUMENTS

| | | | |
|---|---|---|---|
| 2,879,273 | 3/1959 | Asinger et al. | 548/147 |
| 3,816,445 | 6/1974 | Dubs et al. | 426/535 UX |

OTHER PUBLICATIONS

Mussinan et al., "Identification and Flavor Properties of Some 3-Oxazolines and 3-Thiazolines Isolated From Cooked Beef", Abstracts of Papers, 170th National Meeting American Chemical Society, Chicago, Illinois, Aug. 24–29, 1975, Port City Press, Baltimore, Item No. AGFD22.

Primary Examiner—Joseph M. Golian
Attorney, Agent, or Firm—Arthur L. Liberman

[57] ABSTRACT

Described is the use of 2(2'-methylthiopropyl)-4,5-dimethyl-Δ³-thiazoline to augment or enhance the aroma or taste of mashed potato flavor or mashed potato flavored foodstuffs.

2 Claims, 9 Drawing Figures

GC-MS PROFILE FOR EXAMPLE I

I R SPECTRUM FOR EXAMPLE I

GC-MS PROFILE FOR EXAMPLE II

NMR SPECTRUM FOR EXAMPLE II

SOLVENT: CDCL₃
SWEEP WIDTH: 1000 cps.

IR SPECTRUM FOR EXAMPLE II

NMR SPECTRUM FOR EXAMPLE III

SOLVENT: CDCL₃
SWEEP WIDTH: 1000 cps.

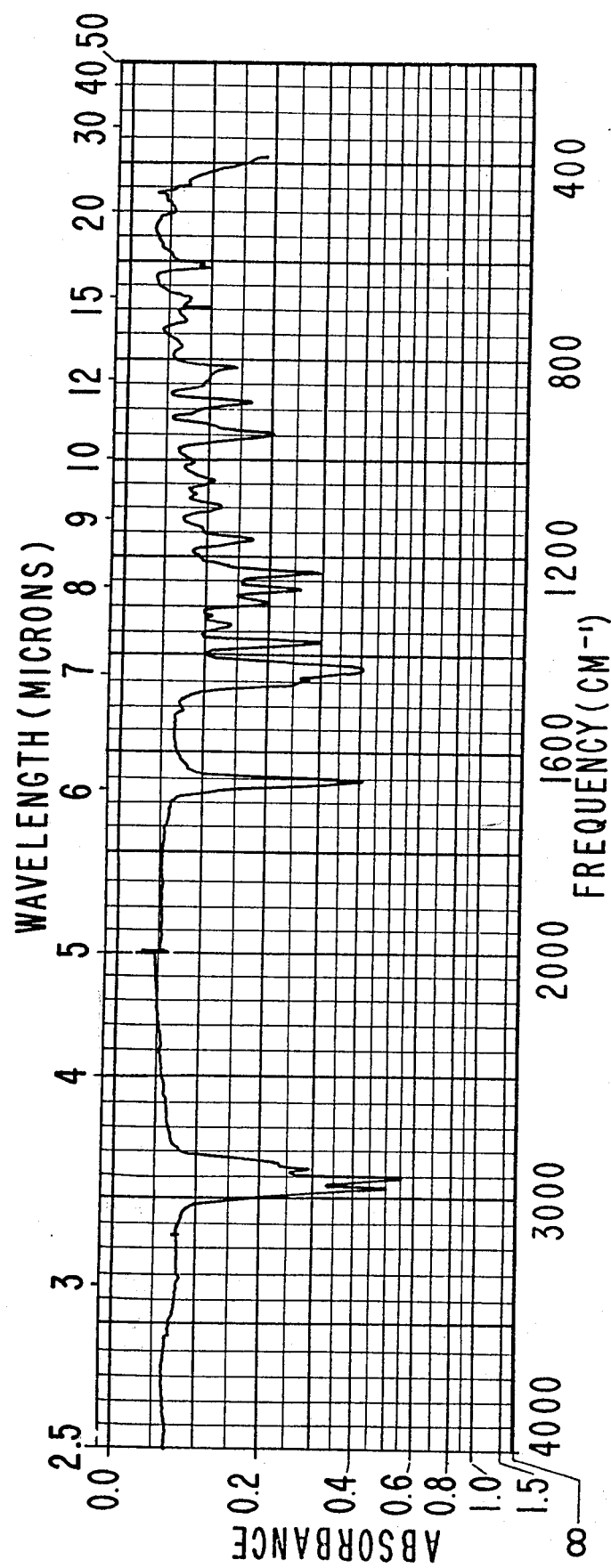

USE OF 2(2'-METHYLTHIOPROPYL)-4,5-DIMETHYL-Δ³-THIAZOLINE TO AUGMENT OR ENHANCE THE AROMA OR TASTE OF MASHED POTATO FLAVOR OR MASHED POTATO FLAVORED FOODSTUFFS

This Application is a divisional of application for U.S. Letters Pat., Ser. No. 017,579 filed on Mar. 5, 1979, which, in turn, is a continuation-in-part of Application for U.S. Letters Pat., Ser. No. 730,156 filed on Oct. 7, 1976, now abandoned.

BACKGROUND OF THE INVENTION

This invention relates to the augmenting or enhancing of the nutty, bready, hydrolyzed vegetable protein, meat extract or vegetable flavor or aroma of foodstuffs initially having such nutty, bready and/or vegetable taste profiles. More particularly, this invention relates to the use of certain 2-alkylthioalkyl-4,5-dialkyl-Δ³-thiazolines to augment or enhance the nutty, bready or vegetable flavor or aroma characteristics of a foodstuff. Contemplated are processes and compositions for augmenting or enhancing the flavor or aroma of foodstuffs.

The term "augment" in its various forms is used herein to mean the supplying, modifying, or imparting of a flavor or aroma characteristic note or nuance to an otherwise bland, relatively tasteless or non-odorous substance or modifying an existing flavor or aroma characteristic where the natural flavor or intrinsic odor is deficient in some regard, or supplementing the existing flavor or aroma impression to modify its quality, character, taste or aroma.

The term "enhance" is used herein to mean the intensification of a flavor or aroma characteristic note or nuance without the modification of the quality thereof. Thus, "enhancement" of a flavor or aroma means that the enhancing agent does not add any additional flavor note or nuance.

As used herein, the term "foodstuffs" includes both solid and liquid ingestible materials which usually do, but need not, have nutritional value. Thus, foodstuffs includes soups, convenience foods, beverages, dairy products, candies, vegetables, cereals, soft drinks, snacks and the like. The term "foodstuffs" is also intended herein to include "medicinal products" and "chewing gum". It is further intended to include such products for human as well as other animal consumption.

As used herein, the term "medicinal products" includes both solids and liquids which are ingestible non-toxic materials which have medicinal value such as cough syrups, cough drops, aspirin and chewing medicinal tablets.

The term "chewing gum" is intended herein to be a foodstuff which is a composition which comprises a substantially water-insoluble, chewable plastic gum base such as chicle, or substitutes therefor, including jelutong, guttakay rubber or certain comestible natural or synthetic resins or waxes. Incorporated with the gum base in admixture therewith may be plasticizers or softening agents, e.g., glycerine; and a flavoring composition which incorporates one or more of the 2-alkylthioalkyl-4,5-dialkyl-Δ³-thiazolines of our invention, and, in addition, sweetening agents which may be sugars, including sucrose or dextrose and/or artificial sweeteners such as cyclamates or saccharin. Other optional ingredients may also be present.

The reproduction of nutty, bready or vegetable flavors or aromas, including tomato and potato flavors has been the subject of a long and continuing search by those engaged in the production of foodstuffs. The shortage of foods, in many parts of the world has given rise to a need for utilizing tasteless or poor-tasting sources of protein and minerals for making such protein and mineral containing foods as palatable as possible. In addition, various techniques utilized in processing foods detract from their flavor quality or give rise to off-flavors. Convenience or "snack" foods are increasing in sales volume worldwide and they require flavoring. Accordingly, materials capable of closely simulating, improving or even exactly duplicating nutty, bready or vegetable flavors or aromas have long been sought.

Sweet, meaty, meat extract-like, beef broth-like, hydrolyzed vegetable protein-like, bread crust-like, potato-like, sulfury, roasted, roasted meat, vegetable and tomato aroma nuances, and the bread crust-like, sweet, meat extract-like, beef broth-like, hydrolyzed vegetable protein-like, salty, bloody, metallic sweet/minty, potato, vegetable, and cooked tomato flavor nuances of foodstuff flavors are particularly desirable for many uses in foodstuff flavors.

Compounds containing the Δ³-thiazoline moiety are disclosed as flavorants in U.S. Pat. No. 3,681,088, issued on Aug. 1, 1972, as well as, U.S. Pat. No. 3,816,445, issued on June 11, 1974. The Δ³-thaizoline moiety has the structure:

U.S. Pat. No. 3,681,088 discloses the preparation of thiazoline compounds having the generic structure:

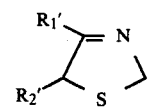

wherein one of $R'_1$ and $R'_2$ represents a primary or secondary hydroxyalkyl or acyloxyalkyl and the other represents hydrogen or alkyl, in order to provide meat, poultry, turkey and breadlike aromas.

U.S. Pat. No. 3,816,445 discloses the use of food flavorants of substituted Δ³-thiazolines compounds having the general formula:

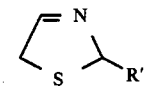

wherein R' can be $C_3$–$C_7$ alkyl, benzyl or 2-methylthioethyl. It is disclosed at column 2, lines 45–50 that such compounds possess vegetable notes such as bean, tomato, pepperoni, asparagus, as well as potato notes. 2(2'methylthioethyl)-Δ³-thiazoline is disclosed in Example IV, at column 3 of U.S. Pat. No. 3,816,445 to display a methional-like, earthy, green, metallic fragrance in the direction of raw potatoes and mushrooms and a greenish flavor in the direction of potatoes, tomatoes, beans and mushrooms. This compound has the structure:

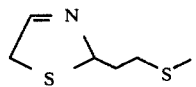

However, the compounds of the instant invention having the structure:

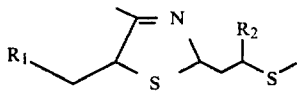

wherein $R_1$ and $R_2$ are the same or different and each represents hydrogen or methyl have unexpected, unobvious and advantageous properties in the field of nutty, bready or vegetable flavor or aromas as applied to foodstuffs.

THE INVENTION

It has now been discovered that novel solid and liquid foodstuff compositions and flavoring compositions for foodstuffs (which initially have nutty, vegetable, hydrolyzed vegetable protein, meat extract and/or bready flavors) having sweet, meaty, meat extract-like, beef broth-like, hydrolyzed vegetable protein-like, bread crust-like, potato-like, sulfury, roasted, roasted meat, vegetable and tomato aroma nuances, and bread crust-like, sweet, meat extract-like, beef broth-like, hydrolyzed vegetable protein-like, salty, bloody, metallic, sweet/meaty, potato, vegetable, and cooked tomato flavor nuances of foodstuff flavors may be provided by the utilization of one or more 2-alkylthioalkyl-4,5-dialkyl-$\Delta^3$-thiazolines having the formula:

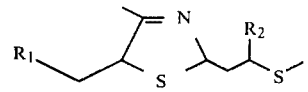

wherein $R_1$ and $R_2$ are the same or different and each is hydrogen or methyl.

Such 2-alkylthioalkyl-4,5-dialkyl-$\Delta^3$-thiazolines may be prepared by first admixing an alkylthioalkanal with aqueous ammonia to form the corresponding amine and then reacting said amine with 3-mercapto-2-butanone or 3-mercapto-2-pentanone in order to produce the desired thiazoline. This reaction sequence is set forth as follows:

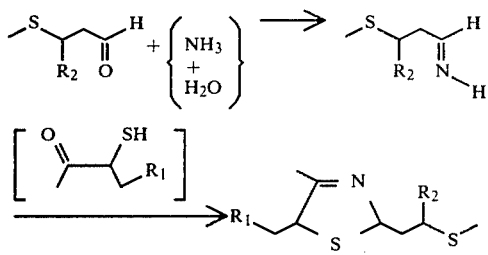

The reaction parameters are exemplified hereinbelow and are also exemplified and stated in U.S. Pat. No. 3,816,445, issued on June 11, 1974, as well as U.S. Pat. No. 2,879,273, issued on Mar. 24, 1959 (wherein the substituent at the "2" position is alkyl rather than alkylthioalkyl).

Specific examples of 2-alkylthioalkyl-4,5-dialkyl-$\Delta^3$-thiazolines produced using the aforementioned process and their flavor properties are as follows (as set forth in Table I, below):

TABLE I

| COMPOUND | STRUCTURE | ORGANOLEPTIC PROPERTIES |
|---|---|---|
| 2(2′Methylthioethyl)-4,5-dimethyl-$\Delta^3$-thiazoline | | A sweet, meaty, meat extract-like, beef broth-like, hydrolyzed vegetable protein-like, and bread crust-like aroma with bread crust-like, sweet, monosodium glutamate like, meat extract-like, beef broth-like hydrolyzed vegetable protein-like, salty, bloody and metallic taste and flavor nuances. |

TABLE I-continued

| COMPOUND | STRUCTURE | ORGANOLEPTIC PROPERTIES |
|---|---|---|
| 2(2'Methylthiopropyl)-4,5-dimethyl-$\Delta^3$-thiazoline | 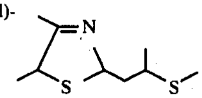 | A sweet, meaty, meat extract-like, beef broth-like, hydrolyzed vegetable protein-like, potato-like aroma with sweet/meaty, meat extract-like, beef broth-like, hydrolyzed vegetable protein-like, metallic, salty and potato-like taste and flavor nuances. |
| 2(2'Methylthioethyl)-4-methyl-5-ethyl-$\Delta^3$-thiazoline | 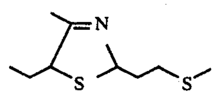 | A sulfury, roasted, roasted meat-like, beef broth-like, vegetable and tomato-like aroma with sulfury, beef broth-like vegetable, metallic and cooked tomato-like taste and flavor nuances. |

When the 2-alkylthioalkyl-4,5-dialkyl-$\Delta^3$-thiazolines of our invention are used as food flavor adjuvants, the nature of the co-ingredients included with each of the said 2-alkylthioalkyl-4,5-dialkyl-$\Delta^3$-thiazolines in formulating the product composition will also serve to augment or enhance the organoleptic characteristics of the ultimate foodstuff treated therewith.

Substances suitable for use herein as co-ingredients or flavoring adjuvants are well known in the art for such use, being extensively described in the relevant literature. It is a requirement that any such material be "ingestibly acceptable", and thus non-toxic or otherwise non-deleterious, particularly from an organoleptic standpoint whereby the ultimate flavor and/or aroma of the consumable material used is not caused to have unacceptable aroma and taste nuances. Such materials in general may be characterized as flavoring adjuvants or vehicles comprising broadly, stabilizers, thickeners, surface active agents, conditioners, other flavorants and flavor intensifiers.

It is a further requirement that such material be organoleptically compatible with the foodstuff with which it is used so that the flavor and aroma nuances of such material, taken together with the flavor and aroma nuances of the foodstuff as a whole give rise to a harmonious and aesthetically pleasing aroma and taste profile.

Stabilizer compounds include preservatives, e.g., sodium chloride, antioxidants, e.g., calcium and sodium ascorbate, ascorbic acid, butylated hydroxy-anisole (mixture of 2- and 3-tertiary-butyl-4-hydroxy-anisole), butylated hydroxy toluene (2,6-di-tertiary-butyl-4-methyl phenol), propyl gallate and the like and sequestrants, e.g., citric acid.

Thickener compounds include carriers, binders, protective colloids, suspending agents, emulsifiers and the like, e.g., agar agar, carageenan; cellulose and cellulose derivatives such as carboxymethyl cellulose and methyl cellulose; natural and synthetic gums such as gum arabic, gum tragacanth; gelatin, proteinaceous materials; lipids; carbohydrates; starches, pectins, and emulsifiers, e.g., mono- and diglycerides of fatty acids, skim milk powder, hexoses, pentoses, disaccharides. e.g., sucrose, corn syrup and the like.

Surface active agents include emulsifying agents, e.g., fatty acids such as palmitic acid, myristic acid and the like, mono- and diglycerides of fatty acids, lecithin, defoaming and flavor-dispersing agents such as sorbitan monstearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include saturated and unsaturated organic amino acids; alcohols including primary and secondary alcohols; esters, carbonyl compounds including ketones and aldehydes; lactones, other cyclic organic materials including benzene derivatives, alicyclics, other heterocyclics such as furans, pyridines, pyrazines, and the like; sulfur-containing materials including thiols, sulfides, disulfides and the like; proteins; lipids; carbohydrates; so-called flavor potentiators such as monosodium glutamate, guanylates, and inosinates; natural flavoring materials such as cocoa, vanilla, and caramel; essential oils and extracts such as anise oil; clove oil, and the like; artificial flavoring materials such as vanillin; and the like.

The specific flavoring adjuvants selected for use may be either solid or liquid depending upon the desired physical form of the ultimate product, i.e., foodstuff, whether simulated or natural, and should, in any event, (i) be organoleptically compatible with the 2-alkylthioalkyl-4,5-dialkyl-$\Delta^3$-thiazoline of our invention by not covering or spoiling the organoleptic properties (aroma and/or taste) thereof; (ii) be non-reactive with the 2-alkylthioalkyl-4,5-dialkyl-$\Delta^3$-thiazoline of our invention; and (iii) be capable of providing an enviroment in which the 2-alkylthioalkyl-4,5-dialkyl-$\Delta^3$-thiazoline can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, to which the flavor and/or aroma are to be imparted, modified, augmented or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of 2-alkylthioalkyl-4,5-dialkyl-$\Delta^3$-thiazoline employed in a particular instance can vary over a relatively wide range, depending upon the desired organoleptic effects to be achieved. Thus, correspondingly greater amounts would be necessary in those instances wherein the ultimate food composition to be flavored is relatively bland to the taste, whereas relatively minor quantitites may suffice for purposes of enhancing a composition merely deficient in natural flavor or aroma. The primary requirement is that the amount selected be effective, i.e., sufficient to augment or enhance the organoleptic characteristics of the parent composition.

The use of insufficient quantities of 2-alkylthioalkyl-4,5-dialkyl-$\Delta^3$-thiazoline will, of course, substantially vitiate any possibility of obtaining the desired results while excess quantities prove needlessly costly and, in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, it is found that quantities of 2-alkylthioalkyl-4,5-dialkyl-$\Delta^3$-thiazoline ranging from a small but effective amount, e.g., 0.005 parts per million up to about 50 parts per million based on total composition are suitable. Concentrations in excess of the maximum quantity stated are not normally recommended, since they fail to provide commensurate enhancement or organoleptic properties. In those instances, when the 2-alkylthioalkyl-4,5-dialkyl-$\Delta^3$-thiazoline is added to the foodstuff as an integral component of a flavoring composition, it is, of course, essential that the total quantity of flavoring composition employed be sufficient to yield to an effective 2-alkylthioalkyl-4,5-dialkyl-$\Delta^3$-thiazoline concentration in the foodstuff product.

Food flavoring compositions prepared in accordance with the present invention preferably contain the 2-alkylthioalkyl-4,5-dialkyl-$\Delta^3$-thiazoline in concentrations ranging from about 0.02% up to about 5% by weight based on the total weight of the said flavoring composition.

The compositions described herein can be prepared according to conventional techniques well known as typified by cake batters and vegetable juice drinks and beverages, and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the 2-alkylthioalkyl-4,5-dialkyl-$\Delta^3$-thiazoline of our invention with, for example, gum arabic, gum tragacanth, carrageenan and the like, and thereafter spray-drying the resultant mixture whereby to obtain the particulate solid product. Pre-prepared flavor mixes in powder form e.g., a vegetable-flavored powder mix are obtained by mixing the dried solid components, e.g., starch, sugar and the like and 2-alkylthioalkyl-4,5-dialkyl-$\Delta^3$-thiazoline in a dry blender until the requisite degree of uniformity is achieved.

It is presently preferred to combine with the 2-alkylthioalkyl-4,5-dialkyl-$\Delta^3$-thiazoline of our invention, the following adjuvants:
Bergamot oil;
Citral;
Amyl alcohol;
5-Phenyl-2-pentenal;
5-Phenyl-4-pentenal;
n-Octanal;
n-Decanal;
Limonene;
Geraniol;
Cadinene;
Dimethylanthranilate;
Amyl butyrate;
2(n-Pentyl)thiazole;
2(i-Propyl)thiazole; 2(n-Propyl)thiazole;
4-Methylthiobutanal;
2-Ethyl-3-acetyl pyrazine;
Tetramethyl pyrazine;
2-Methyl pyrazine;
2-Trans hexenal;
Maltol;
2-Phenyl-4-pentenal;
2-Phenyl-4-pentenal dimethyl acetal;
2-Phenyl-4-pentenal diethyl acetal;
2($\beta$-hydroxyethyl)thiazole;
2-Methyl butanethiol;
4-Mercapto-2-butanone;
3-Mercapto-4-pentanone;
1-Mercapto-2-propanone;
Furfural;
Furfuryl alcohol;
2-Mercapto propionic acid;
2-Ethyl-3-methyl pyrazine;
Tetramethyl pyrazine;
Polysulfides;
Dipropyl disulfide;
Methyl benzyl disulfide;
2-Butyl thiophene;
2,3-Dimethyl thiophene;
5-Methyl furfural;
2-Acetyl furan;
2,5-Dimethyl-3-acetyl furan;
2,4-Decadienal;
Guaiacol;
Phenyl acetaldehyde;
$\delta$-Decalactone;
d-Limonene;

Acetoin;
Amyl acetate;
Ethyl butyrate;
Levulinic acid;
Piperonal;
Ethyl acetate;
n-Pentanal;
Hexanal;
Diacetyl;
Monosodium glutamate;
Cysteine;
Hydrolyzed vegetable protein;
Hydrolyzed fish protein;
Vanillin;
Methyl furoate;
Methyl cyclopentenolone;
Pyruvic acid;
Isoamyl levulinate;
Ethyl anthranilate;
Orange oil;
Ethyl heptanoate;
Acetoin;
Butyl butyryl lactate;
Ethyl vanillin;
Ethyl butyrate;
Rose oil;
Benzyl acetate;
Tolyl aldehyde;
α-ionone;
Para-tolylacetaldehyde;
Heliotropin;
Butyric acid;
Acetylmethylcarbinol;
Methional
2-(2-methylthioethyl)-$\Delta^3$-thiazoline;
Alcohol;
Acetaldehyde;
i-Valeric acid;
Caprylic acid;
Benzaldehyde;
i-Valeraldehyde;
Butyric acid;
Propionic acid;
Phenylacetaldehyde;
Linalool;
Dimethylsulphide;
Terpinylbutyrate;
Cis-3-hexenol;
Phenylacetic acid guaiacyl ester;
Methylheptenone;
Caproaldehyde;
2-Isobutyl thiazole; and
2-n-Butyl thiazole.

The following examples are intended to illustrate the instant invention. It will be understood that these examples are illustrative and that the invention is to be considered restricted thereto only as indicated in the appended claims.

All parts and percentages given herein are by weight unless otherwise specified.

EXAMPLE I

PREPARATION OF 2(2'METHYLTHIOETHYL)-4,5-DIMETHYL-$\Delta^3$-THIAZOLINE

Reaction

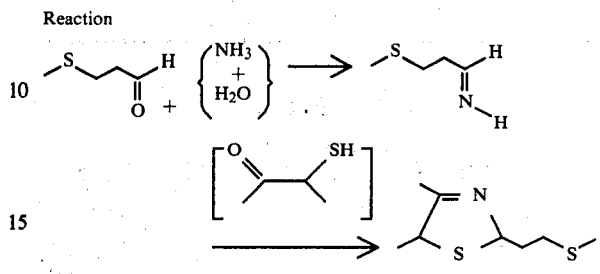

Into a 500 ml, three-necked, round-bottom flask, equipped with mechanical stirrer, 250 ml addition funnel, thermometer, Friedrichs condenser and ice-bath is placed 45.2 ml of a 58% aqueous ammonia solution and 45 ml distilled water. Dropwise, with stirring, while maintaining the temperature at 25°–28° C., 52 gms of methional is added to the ammonia solution. After the methional is added, dropwise, with stirring, over a period of one hour, 104 gms of a 50% solution of 3-mercapto-2-butanone in 95% ethanol is added. The resulting reaction mass is kept at room temperature with stirring during the addition of the 3-mercapto-2-butanone. The reaction mass is then extracted with two 100 ml portions of diethyl ether. The diethyl ether extracts are combined and washed with three 100 ml portions of distilled water and then dried over anhydrous sodium sulfate. The dried extracts are then evaporated on a rotary evaporator and the resulting oil is distilled on a 6" Vigreux column at a vapor temperature of 97°–103° C., a liquid temperature of 129°–140° C. and a pressure of 2 mm Hg.

The Mass spectrum is set forth in FIG. 1. The NMR spectrum is set forth in FIG. 2. The infra-red spectrum is set forth in FIG. 3.

The NMR analysis is as follows:

| 1.5 ppm (doublet of doublets) | $CH_3-\overset{\overset{\displaystyle C=C}{\mid}}{C}-S-$ | 3H |
|---|---|---|
| 2.08 (d, J = 2H$_z$) | $CH_3-C=N-$ | |
| 2.13 (s) | $CH_3-S-$ | 8H |
| 2.46–1.86 (m) | methylene methine | |
| 2.66 (t) | $-CH_2-S-$ | 2H |
| 4.28 (m) | $\underset{\underset{\displaystyle C=C=}{\mid}}{HC-S}$ | 1H |
| 5.62 (m) | $\underset{\underset{\displaystyle S}{\mid}}{HC-N=C}$ | 1H |

The infra-red analysis is as follows:
880 cm$^{-1}$, 940, 1160, 1220, 1240, 1280, 1370, 1430, 1660, 2920, 2960.

The Mass Spectral analysis is as follows:

| M/E | Relative Intensity |
|---|---|
| 55 | 13 |
| 61 | 19 |
| 68 | 18 |
| 87 | 30[4] |
| 100 | 21[5] |

-continued

| M/E | Relative Intensity |
|---|---|
| 114 | 32[3] |
| 126 | 21[6] |
| 128 | 16 |
| 174 | 100[1] |
| M189 | 44[2] |

EXAMPLE II

PREPARATION OF 2(2′METHYLTHIOPROPYL)-4,5-DIMETHYL-Δ³-THIAZOLINE

Reaction:

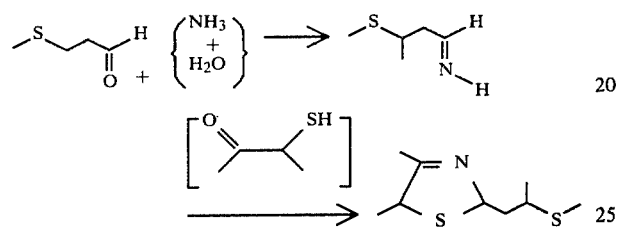

Into a 500 ml, three-necked, round bottom-flask, equipped with mechanical stirrer, thermometer, Friedrichs condenser, 250 ml addition funnel and cooling bath, is placed 87 ml of a 30% aqueous ammonia solution. The ammonia solution is cooled to a temperature of between 13° and 17° C. and, dropwise, with stirring, 59.1 gms of 3-methylmethional is added. The reaction mass is stirred for a period of 90 minutes, after which time 106 gms of a 50% solution (in 95% ethanol) of 3-mercapto-2-butanone is added over a 30 minute period, dropwise. The reaction mass is maintained during the addition at a temperature of between 11° and 16° C. After the addition, the reaction mass is permitted to warm up to 25° C. and is stirred for an additional 2.5 hours. The reaction mass is then transferred to a separatory funnel and is observed to exist in two phases; an oil phase and an aqueous phase. The oil phase is drawn off and the aqueous phase is extracted with three 100 ml portions of diethyl ether. The ether extracts and the oil phase are then combined and dried over anhydrous sodium sulfate and then stripped of solvent on a rotary evaporator. The product is then distilled on a 8″ Vigreux column at a vapor temperature of 100°–104° C. and a pressure of 2 mm Hg.

The resulting material is confirmed by GLC, NMR, IR and Mass Spectral analyses to have the structure:

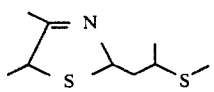

The Mass spectrum is set forth in FIG. 4. The NMR spectrum is set forth in FIG. 5. The infra-red spectrum is set forth in FIG. 6.

The NMR analysis is as follows:

| 1.34 ppm (doublet of doublets) | CH₃—C—S | 3H |
|---|---|---|

-continued

| 1.50 (d) | $CH_3-\underset{S}{C}-C=N$ | 3H |
|---|---|---|
| 2.45–1.55 (m) | —CH₂— | 2H |
| 2.53 (m) | CH₃CH—S— | 1H |
| 4.25 (m) | $CH_3-\underset{C=N}{CH}-S-$ | 1H |
| 5.90 (m) | $HC-N=C$<br>$\;\;\vert$<br>$\;\;S-$ | 1H |

The infra-red analysis is as follows:
940 cm⁻¹, 1245, 1370, 1430, 1440, 1660, 2920, 2960.
The Mass Spectral analysis is as follows:

| M/E | Relative Intensity |
|---|---|
| 55 | 20 |
| 75 | 47[4] |
| 87 | 40 |
| 89 | 20 |
| 100 | 22 |
| 114 | 45[6] |
| 122 | 47[5] |
| 140 | 61[3] |
| 188 | 100[1] |
| M203 | 66[2] |

EXAMPLE III

PREPARATION OF 2(2′METHYLTHIOETHYL)-4-METHYL-5-ETHYL-Δ³-THIAZOLINE

Reaction:

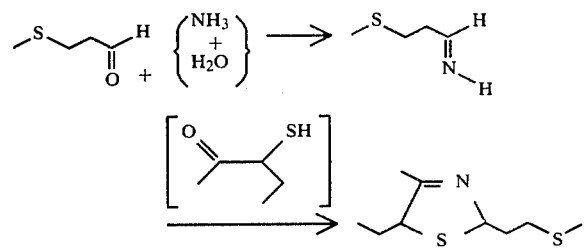

Into a 1-liter reaction flask, equipped with mechanical stirrer, Friedrichs condenser, thermometer, isopropanol/dry-ice bath, and 250 ml addition funnel is placed 145.8 ml of a 30% aqueous ammonia solution. The solution is maintained at 5°–15° C. and over a period of 45 minutes, dropwise, with stirring, is added 105.5 gms of methional. After the methional is added, 253.9 gms of a 50% 3-mercapto-2-pentanone solution (in 95% aqueous ethanol) is added to the reaction mass over a period of two hours while maintaining the reaction mass at 10°–15° C. After the addition of the 3-mercapto-2-pentanone, the temperature of the reaction mass is permitted to rise to 25° C. and is maintained at 25° C. for a period of 1.5 hours with stirring. The reaction mass is then transferred to a separatory funnel and 100 ml of a saturated aqueous sodium chloride solution is added thereto. The reaction phase now exists in two phases: an oil phase and an aqueous phase. The oil phase is separated from the aqueous phase and the aqueous phase is extracted with three 100 ml portions of diethyl ether. The ether extracts and the oil phase are then combined and washed with two 100 ml portions of saturated aqueous sodium chloride solution. The resulting organic phase is then dried over anhydrous sodium sulfate, stripped of ether on a rotary evaporator and distilled on a 12" Vigreux column at 174° C. and 22 mm Hg pressure.

GLC, NMR, IR and Mass Spectral analyses confirm that the compound has the structure:

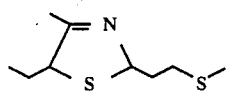

This material has a threshold level of 0.005 ppm and a use level at a concentration of 0.01 ppm and at this use level yields a sulfury, roasted, roasted meat-like, beef broth-like, vegetable and tomato aroma with a sulfury beef broth-like, vegetable, metallic and cooked tomato-like flavor character.

The Mass spectrum is set forth in FIG. 7. The NMR spectrum is set forth in FIG. 8. The infra-red spectrum is set forth in FIG. 9.

The NMR analysis is as follows:

| 0.94 | $CH_3$ | 3H |
|---|---|---|
| 2.02 | $CH_3-C=N-$ | |
| 2.06 | $CH_3-S$ | 12H |
| 2.36–2.00 | $-CH_2-$ | |
| 4.24 | $\underset{HC-S}{C=}$ | 1H |
| 5.52 | $-S-HC-N=$ | 1H |

The infra-red analysis is as follows:
945 cm$^{-1}$, 1230, 1260, 1370, 1430, 1660, 2920, 2960.

EXAMPLE IV

A walnut flavor formulation is prepared by blending the following ingredients:

| INGREDIENTS | PARTS BY WEIGHT |
|---|---|
| Vanillin | 4.0 |
| Ethyl-2-methylbutyl | 1.0 |
| Butyl isovalerate | 4.0 |
| 2,3-Diethyl pyrazine | 0.5 |
| Methyl cyclopentenolone | 8.0 |
| α-Hydroxy-β-methyl-Δ,α,β-γ-hexenolactone | 2.0 |
| Benzaldehyde | 6.0 |
| Valerian oil Indonesian (0.1% solution in propylene glycol) | 0.5 |
| Propylene glycol | 74.0 |

This walnut flavor is compared in water at the rate of 10 ppm with the identical flavor to which 0.5 parts of 2(2'methylthioethyl)-4-methyl-5-ethyl-Δ$^3$-thiazoline prepared according to Example III is added. The flavor containing 2(2'methylthioethyl)-4-methyl-5-ethyl-Δ$^3$-thiazoline has a fuller, more natural walnut kernel-like taste because of the addition to the formulation of said thiazoline compound.

EXAMPLE V

A walnut flavor is prepared by blending the following ingredients:

| INGREDIENTS | PARTS BY WEIGHT |
|---|---|
| Vanillin | 4.0 |
| Ethyl-2-methylbutyrate | 1.0 |
| Butyl isovalerate | 4.0 |
| 2,3-diethyl pyrazine | 0.5 |
| Methyl cyclopentenolone | 8.0 |
| α-Hydroxy-β-methyl-Δ-α,β-γ-hexenolactone | 2.0 |
| Benzaldehyde | 6.0 |
| Valerian Oil Indonesian (0.1% solution in propylene glycol) | 0.5 |
| Propylene glycol | 74.0 |

This walnut flavor is compared in water at the rate of 10 ppm with the same flavor to which 2% 2(2'1 methylthioethyl)-4,5-dimethyl-Δ$^3$-thiazoline prepared according to Example I is added. The flavor containing the 2(2'methylthioethyl)-4,5-dimethyl-Δ$^3$-thiazoline has a sweeter, more walnut kernel and rounded taste and is therefore improved.

EXAMPLE VII

VEGETABLE FLAVOR FORMULATION

2(2'Methylthioethyl)-4-methyl-5-ethyl-Δ$^3$-thiazoline prepared according to Example III is added directly to a food product prior to processing and canning. The following illustrates the beneficial flavor effect when 2(2'methylthioethyl)-4-methyl-5-ethyl-Δ$^3$-thiazoline prepared according to Example III is added to several food products just prior to their consumption:

(i) In blended vegetable sauce at approximately 30 ppm: Brings out the cooked vegetable note with tomato nuances.
(ii) In vegetable soup at 40 ppm: Imparts a cooked vegetable flavor. The cooked notes give the entire vegetable flavor a fuller body.
(iii) In bean tomato sauce at approximately 20 ppm: Modifies the flavor by reducing the harsh character of the tomato spice mixture while at the same time adding cooked vegetable notes and developing the "cooked" tomato note.

The levels of concentration of the 2(2'methylthioethyl)-4-methyl-5-ethyl-Δ$^3$-thiazoline prepared according to Example III may be reduced by 25% when 2-isobutyl thiazole is added at the rate of 5 ppm in addition to the 2(2'methylthioethyl)-4-methyl-5-ethyl-Δ$^3$-thiazoline to the various products set forth above. It should be understood that noticeable difference in the flavor are discernable at other concentrations.

EXAMPLE VIII

USE OF 2(2'METHYLTHIOETHYL)-4-METHYL-5-ETHYL-Δ$^3$-THIAZOLINE TO ENHANCE THE VEGETABLE FLAVOR OF VEGETARIAN VEGETABLE SOUP

2(2'Methylthioethyl)-4-methyl-5-ethyl-Δ$^3$-thiazoline prepared according to Example III is added at the rate of 2 ppm to condensed Vegetarian Vegetable Soup (Shop-Rite ® Brand). One liter of water is added to one liter of soup and thoroughly admixed. The resulting mixture is then simmered (200° F.) for a period of 10 minutes. The resulting soup is compared by a bench panel with a soup which has no 2(2'methylthioethyl)-4-methyl-5-ethyl-Δ$^3$-thiazoline added thereto. The soup having the 2(2'methylthioethyl)-4-methyl-5-ethyl-Δ$^3$-thiazoline prepared according to Example III is unanimously preferred as having a more vegetable-like taste with fuller mouthfeel and better aroma, and in addition, pleasant cooked tomato nuances.

EXAMPLE VI

A mashed potato flavor is produced by intimately admixing the following ingredients:

| INGREDIENTS | PARTS BY WEIGHT |
|---|---|
| Vanillin | 2.0 |
| Diacetyl | 3.0 |
| Butyrate acid | 3.0 |
| Acetyl methyl carbinol | 5.0 |
| Methional | 10.0 |
| 2(2′Methylthiopropyl)-4,5-dimethyl-$\Delta^3$-thiazoline | 30 |
| 95% food grade aqueous ethanol | 900 |

The addition of the 2(2′methylthiopropyl)-4,5-dimethyl-$\Delta^3$-thiazoline in the above flavor formulation lends an excellent baked potato nuance to this formulation causing it to have the property of imparting a baked potato nuance to a standard commercial mashed potato when the formulation is added thereto at the rate of 5 ppm (rate of $\Delta^3$-thiazoline:0.15 ppm).

EXAMPLE VII

Test solutions of the following materials are compared from an organoleptic standpoint:

(i) 2-(2-(methylthio)ethyl)-3-thiazoline having the structure:

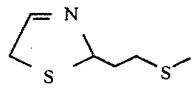

prepared according to Example IV set forth at column 3, lines 69–75 and column 4, lines 1–4 of U.S. Pat. No. 3,816,445;

(ii) 2(2′methylthioethyl)-4,5-dimethyl-$\Delta^3$-thiazoline having the structure:

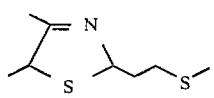

prepared according to the process of Example I on page 22, supra.

(iii) 2,4,5-trimethyl-$\Delta^3$-thiazoline having the structure:

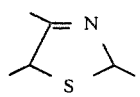

prepared by reacting 2-mercapto-3-butanone with acetaldehyde amine according to the following procedure:

120 ml of 30% aqueous ammonia and 120 ml distilled water are placed in a 300 cc, three-necked flask, equipped with an immersion thermometer, a mechanical stirrer, a cold addition funnel and a water-cooled condenser. The temperature of the aqueous ammonia is lowered to 10°–20° L C. with a wet ice bath, and 60 grams of freshly distilled acetaldehyde is added dropwise with stirring over a one-hour period. The temperature is maintained at 10°–20° L C. 41.5 Grams of 3-mercapto-2-butanone is added dropwise over a one-hour period with stirring. After addition, the reaction mass is stirred for a period of three hours at room temperature. The reaction mass is then stean distilled and approximately 250 cc product are collected. The stream distillate is then intimately admixed with saturated salt solution and then extracted with three 50 ml portions diethyl ether. The diethyl ether extract is then dried over anhydrous sodium sulfate and concenrated on a rotary evaporator. Preparative GLC (second peak) yields the product, 2,4,5-trimethyl-$\Delta^3$-thiazoline.

In various concentrations each of the test compounds is added to water or ethanol or a mixture thereof thereby formulating test solutions and the taste of each of the test solutions (of equal intensity) is as follows:

compound (ii) at 0.5 ppm is compared with Compound (i) at 0.025 ppm. At these levels, both chemicals have the same flavor strength. Compound (ii) has a sweet, beef broth, hydrolyzed vegetable protein, meat extract, cooked vegetable (not cabbage), carrot-like aroma and taste with pleasant light metallic undertones. Compound (i) has a light, sulfury, very metallic, bloody aroma with strong metallic, tomato puree, pineapple metallic taste having a weak hydrolyzed vegetable protein, brothy undertone. Although both compounds have similar notes, the strengths are completely different and compound (ii) is especially suitable for hydrolyzed vegetable protein and meat extract flavors but compound (i) is especially suitable for tomato and pineapple flavors. In addition, compound (i) seems to be substantially stronger. Accordingly, these chemicals are considered to be unexpectedly different. Furthermore, the vegetable notes are completely missing in compound (i); as to compound (iii), insofar as its flavor and aroma are concerned, it has liver-like and fresh chopped meat-like notes with a light sour effect at 0.2, 0.5 and 1.0 ppm, and the taste of compound (iii) is chemical at 2.0 ppm.

In view of the foregoing, the compound having the structure:

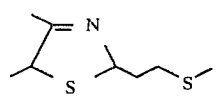

is unexpectedly, unobviously and advantageously useful for imparting, enhancing or modifying hydrolyzed vegetable protein and meat extract flavors, given the flavor properties of the compound having the structure:

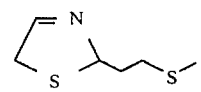

which is not useful for hydrolyzed vegetable protein or meat extract flavors but is only useful for tomato and pineapple flavors; and given the flavor properties of the compound having the structure:

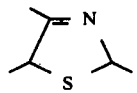

which is also not useful for hydrolyzed vegetable protein flavors and which has little if any use for meat extract flavors, but is only useful at relatively low levels in liver and chopped meat flavor. Furthermore, given cojointly the flavor properties of the two compounds of the prior art having the structure:

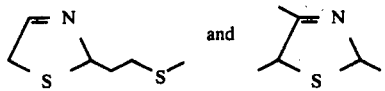

the flavor properties of the compound having the structure:

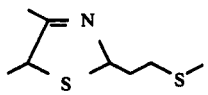

are unexpectedly unobvious and advantageous insofar as their uses for imparting, enhancing or modifying hydrolyzed vegetable protein and meat extract flavors are concerned.

BRIEF DESCRIPTION OF THE DRAWINGS

FIG. 9 represents the Infra-red spectrum for 2(2methylthioethyl)-4-methyl-5-ethyl-$\Delta^3$-thiazoline produced according to Example III.

Figure 1:
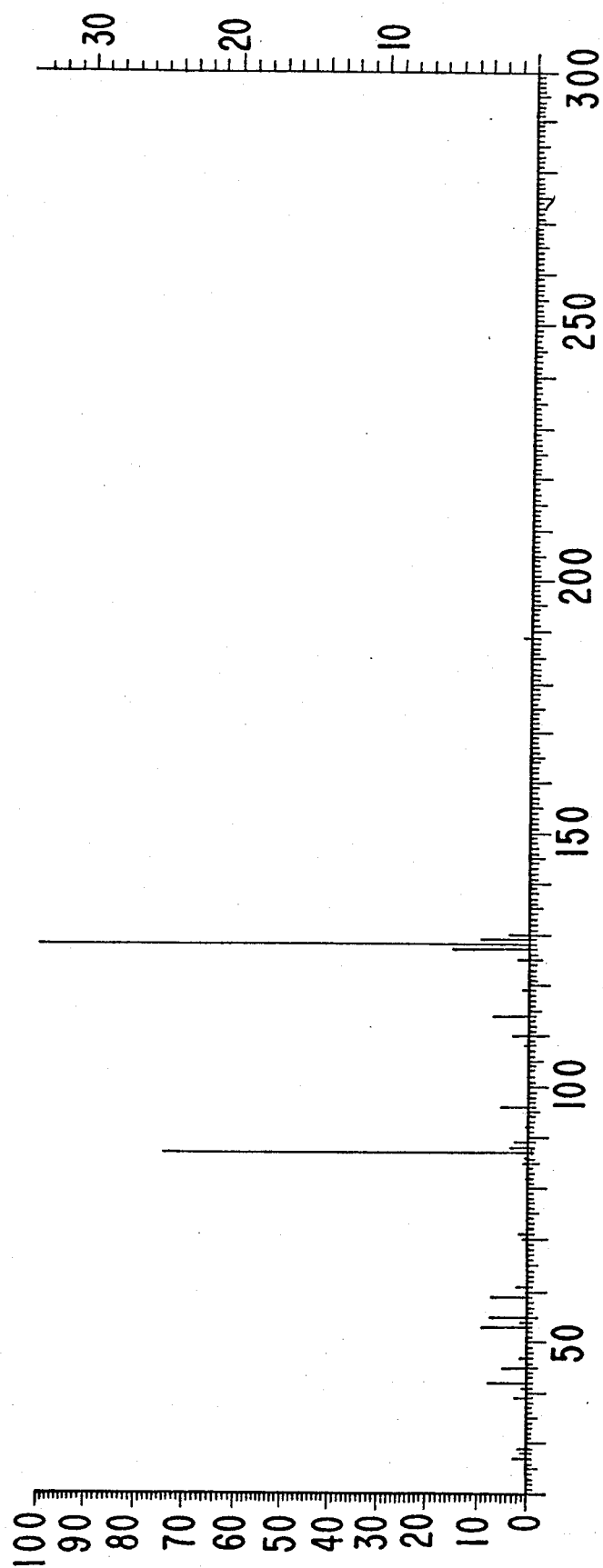
FIG. 1 represents the Mass spectrum for 2(2'methylthioethyl)-4,5-dimethyl-$\Delta^3$-thiazoline produced according to Example I.
Figure 2:
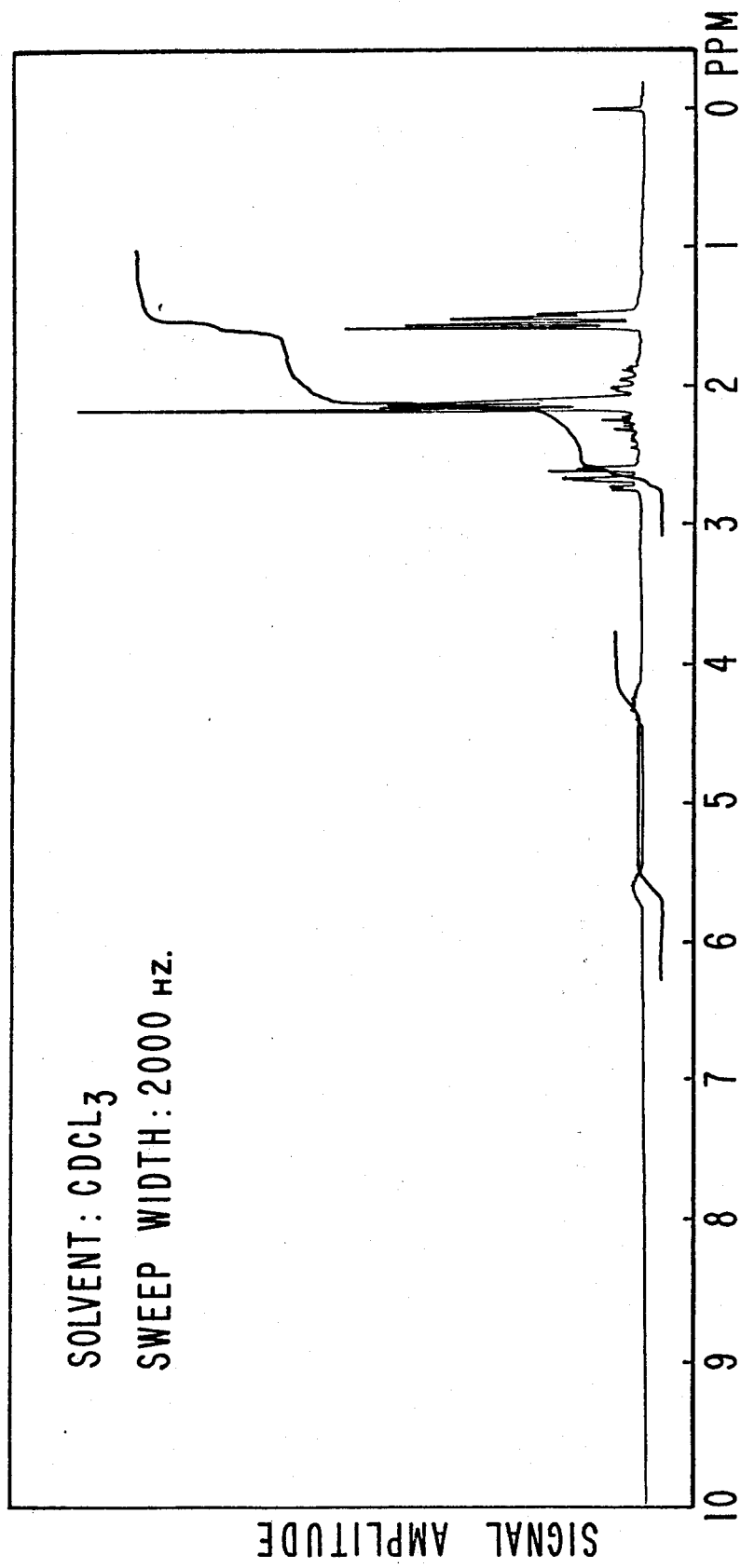
FIG. 2 represents the NMR spectrum for 2(2'methylthioethyl)-4,5-dimethyl-$\Delta^3$-thiazoline produced according to Example I.
Figure 3:
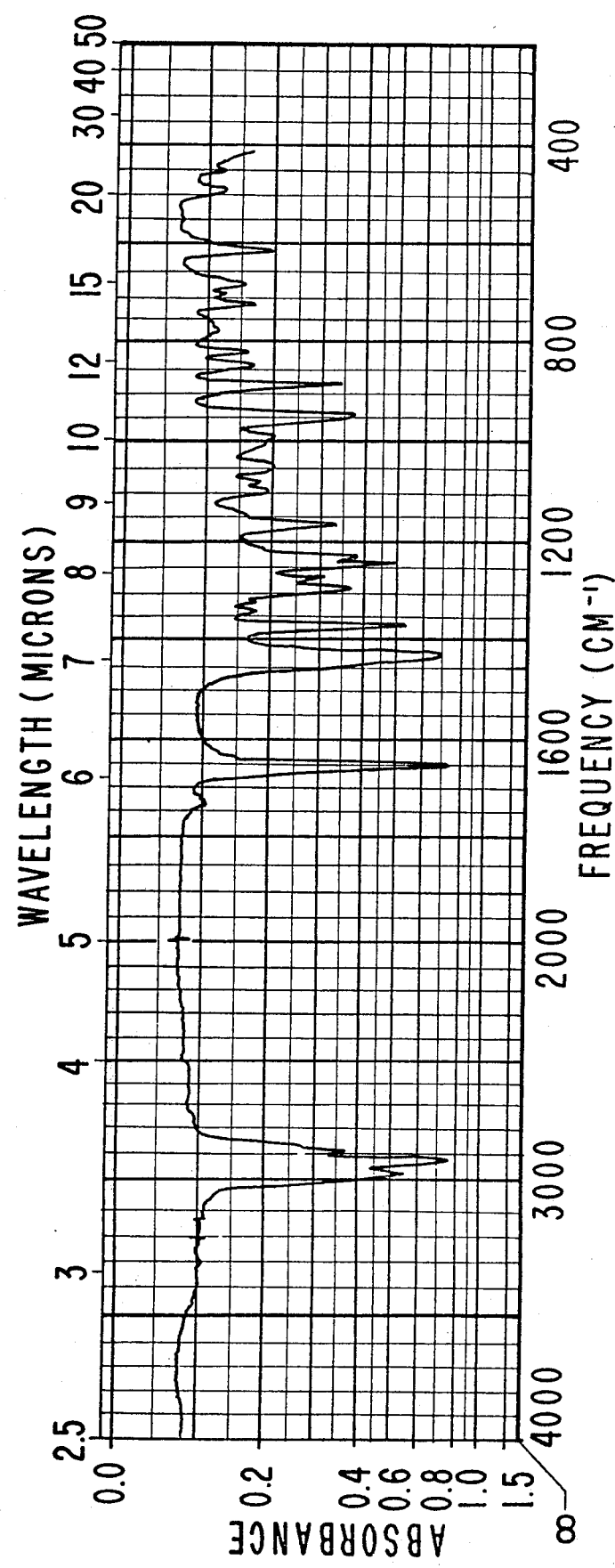
FIG. 3 represents the Infra-red spectrum for 2(2'methylthioethyl)-4,5-dimethyl-$\Delta^3$-thiazoline produced according to Example I.
Figure 4:
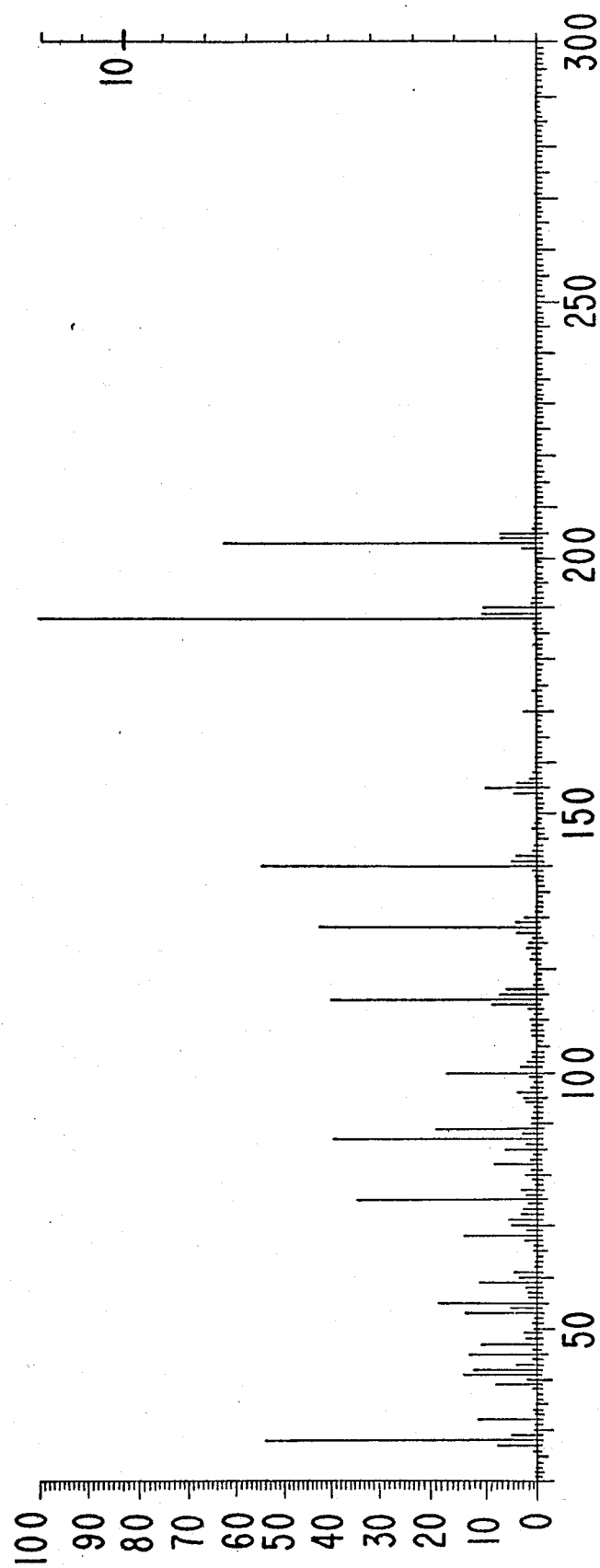
FIG. 4 represents the Mass spectrum for 2(2'methylthiopropyl)-4,5-dimethyl-$\Delta^3$-thiazoline produced according to Example II.
Figure 5:
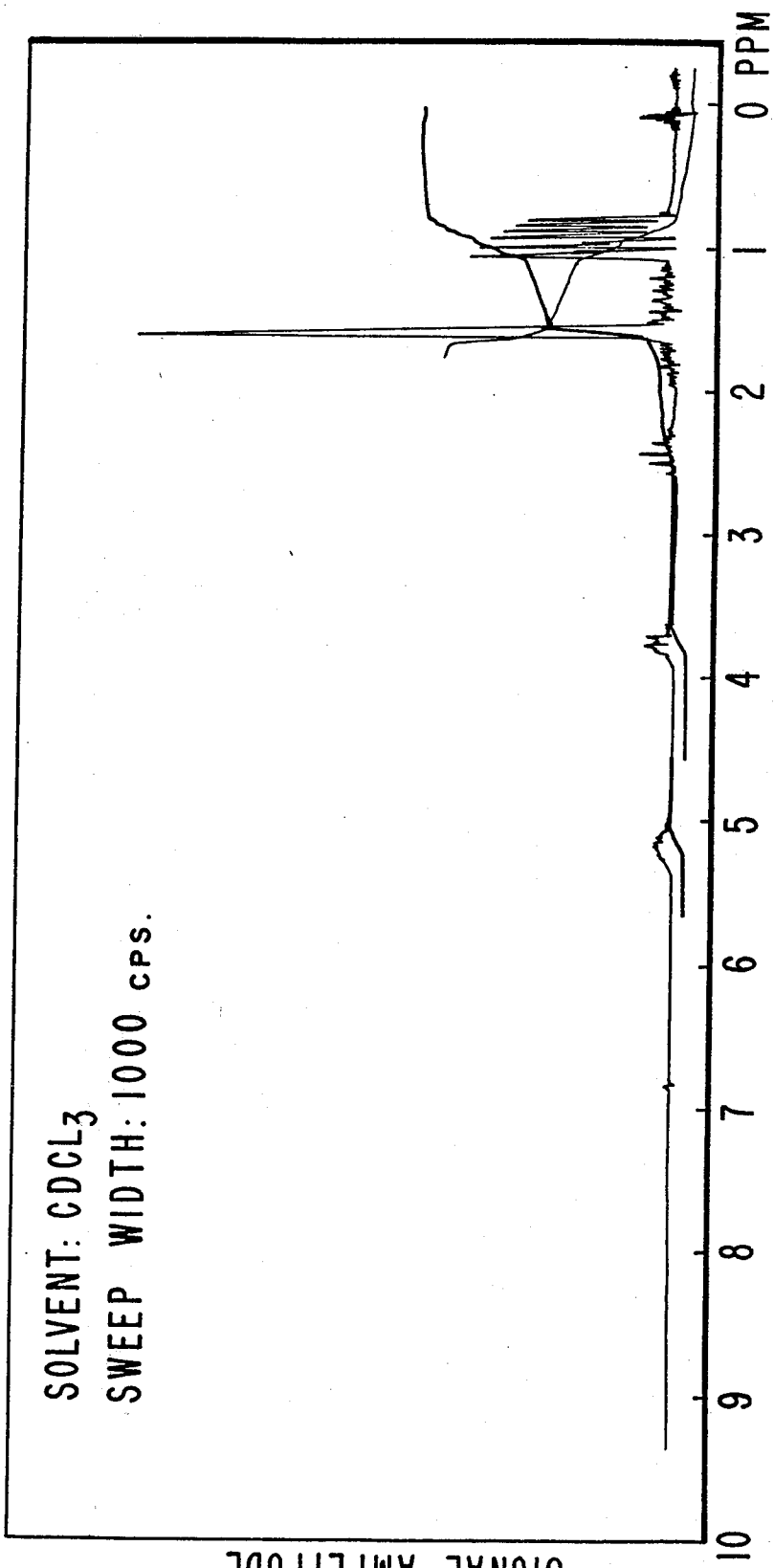
FIG. 5 represents the NMR spectrum for 2(2'methylthiopropyl)-4,5-dimethyl-$\Delta^3$-thiazoline produced according to Example II.
Figure 6:
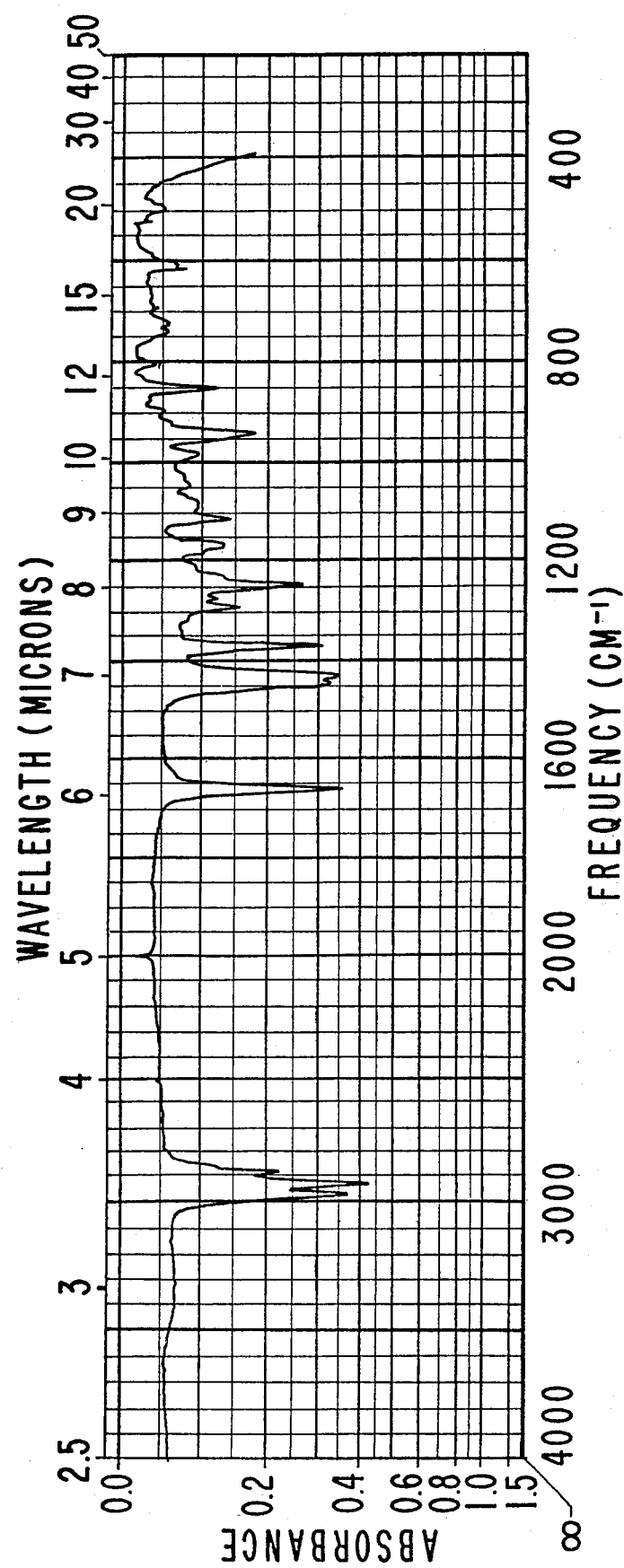
FIG. 6 represents the Infra-red spectrum for 2(2'methylthiopropyl)-4,5-dimethyl-$\Delta^3$-thiazoline produced according to Example II.
Figure 7:
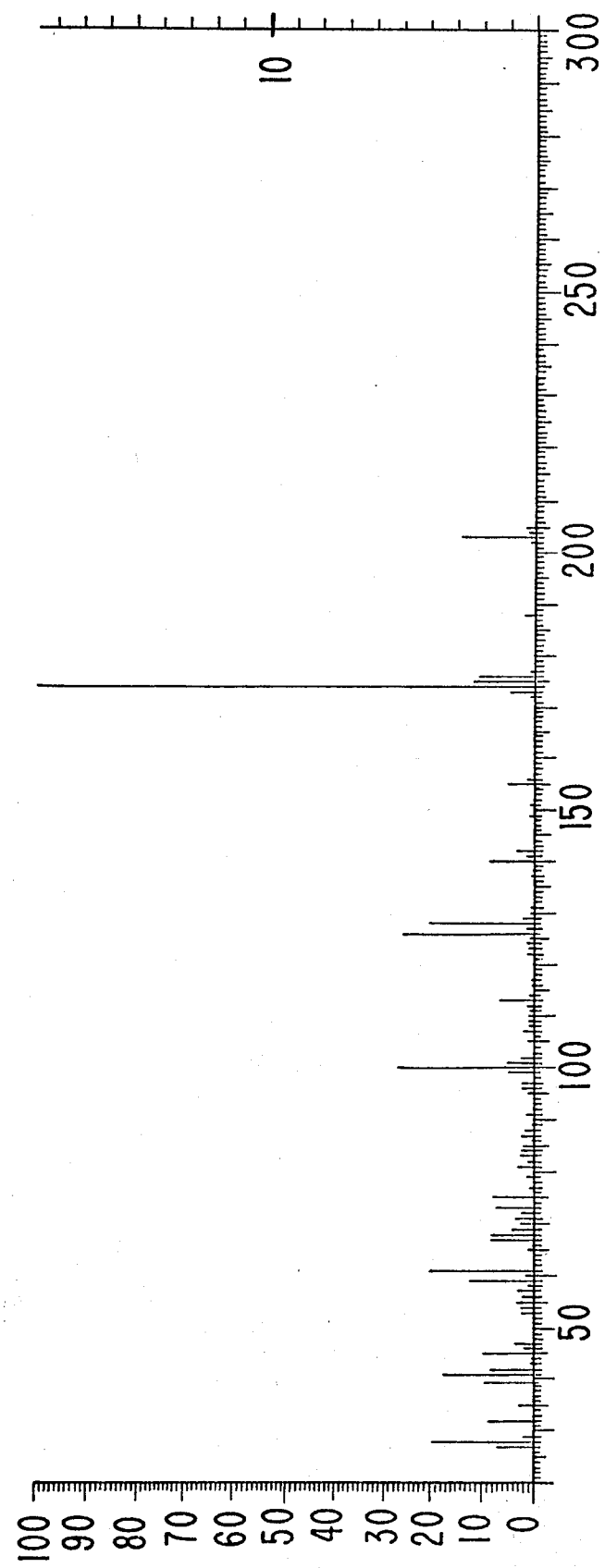
FIG. 7 represents the Mass spectrum for 2(2'methylthioethyl)-4-methyl-5-ethyl-$\Delta^3$-thiazoline produced according to Example III.
Figure 8:
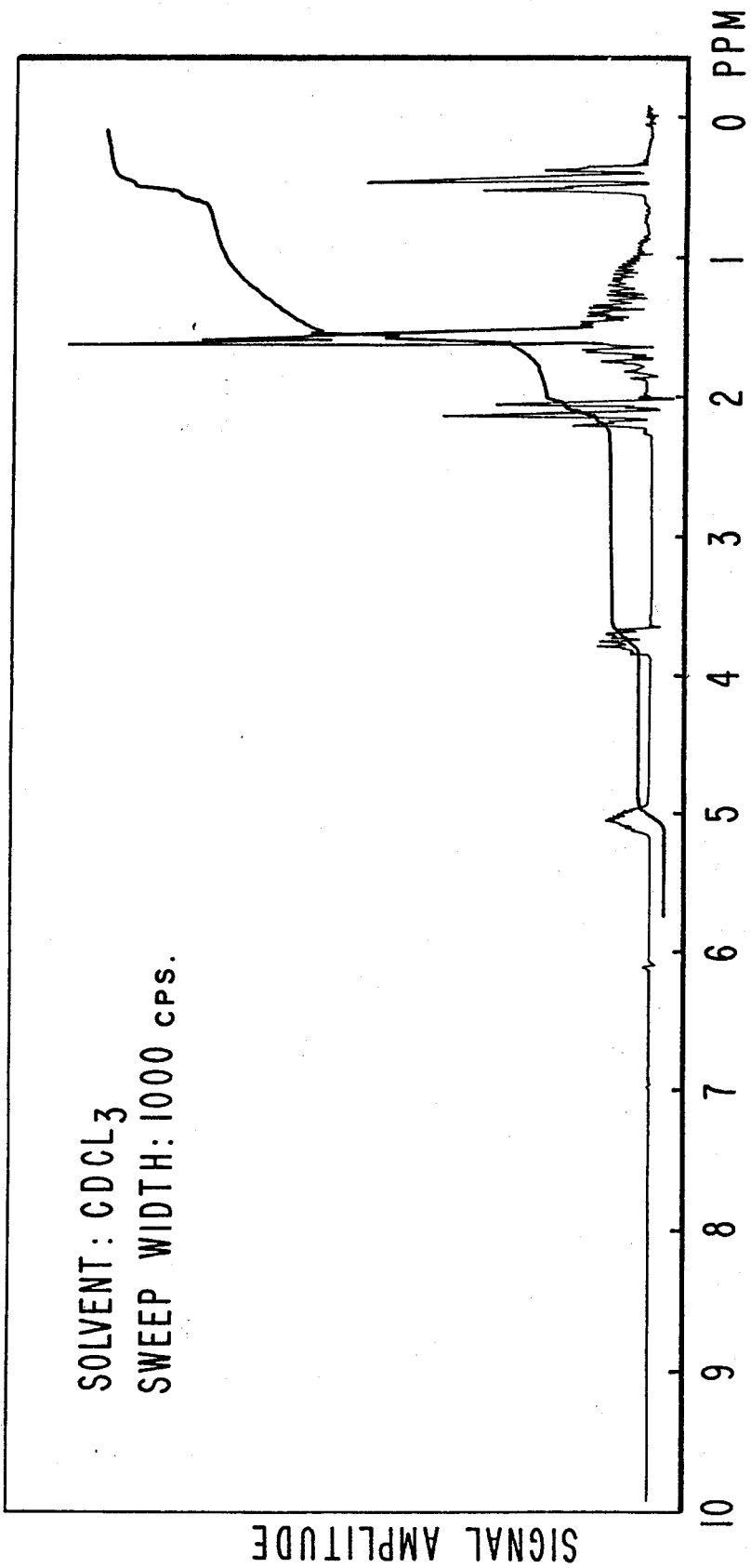
FIG. 8 represents the NMR spectrum for 2(2'methylthioethyl)-4-methyl-5-ethyl-$\Delta^3$-thiazoline produced according to Example III.

What is claimed is:

1. A method for augmenting or enhancing the aroma or taste of mashed potatoes comprising the step of adding to said mashed potatoes from 0.005 parts per million up to about 50 parts per million based on the total weight of said mashed potatoes of 2(2'-methylthiopropyl)-4,5-dimethyl-$\Delta^3$-thiazoline.

2. The process of claim 1 with the amount of 2(2'-methylthiopropyl)-4,5-dimethyl-$\Delta^3$-thiazoline in the mashed potatoes is 0.15 parts per million.

* * * * *